United States Patent [19]

Brenner

[11] 3,956,113

[45] May 11, 1976

[54] PROCESS FOR THE MANUFACTURE OF AMINO COMPOUNDS FIXED TO CARRIERS

[76] Inventor: Max Brenner, Spiegelbergstrasse 33, CH-4059 Basel, Switzerland

[22] Filed: Nov. 23, 1973

[21] Appl. No.: 418,238

[30] Foreign Application Priority Data
Nov. 22, 1972 Switzerland.................... 17021/72
Nov. 8, 1973 Switzerland.................... 15692/73

[52] U.S. Cl.............................. 260/112 R; 195/68; 210/22 R; 260/112.5 R
[51] Int. Cl.²........................................ B01D 13/00
[58] Field of Search................ 210/22, 321, 500 M; 260/112 R, 233.3 R; 424/94; 195/63, 68, DIG. 11

[56] References Cited
UNITED STATES PATENTS 3,281,331  10/1966  Bergkvist.......................... 424/94 X
3,403,146  9/1968  Hunt............................ 260/233.3 R
3,645,852  2/1972  Axen et al....................... 260/112 R
3,674,767  7/1972  Lilly et al..................... 195/DIG. 11

*Primary Examiner*—Frank A. Spear, Jr.
*Attorney, Agent, or Firm*—Wenderoth, Lind & Ponack

[57] ABSTRACT

Process of fixing peptide-type compounds to a carrier by reacting a cyanide compound and a reagent containing positive halogen with a polyhydroxy compound in an alkaline medium, removing low molecular components from the resultant reaction mixture, reacting the cross-linked activated product thus obtained with a water-soluble amino compound capable of substitution on at least one basic nitrogen atom, and subjecting the reaction mixture to dialysis or filtration.

28 Claims, No Drawings

PROCESS FOR THE MANUFACTURE OF AMINO COMPOUNDS FIXED TO CARRIERS

The fixing of substances of a peptide nature (for example peptide hormones, enzymes or antibodies) to preferably insoluble carriers has already been studied for a considerable time, because of its interesting and diverse possible applications; [Grubhofer and Scheith, Z, Physiol, Chem. (Hoppe Seyler) 297, 108 (1954); Micheel and Ewers, Markromol, Chem., 3, 200 (1949); Levin, Pecht, Goldstein and Katchalski, Biochemistry 3, 1905 (1964); Weetall and Weliky, Nature 204, 896 (1964)]. Endeavours in this direction which followed the first publications have been recorded in extensive patent literature.

In practice, the fixing to polysaccharides and polysaccharide derivatives proved particularly successful; this circumstance presumably is related to the nature of the interaction between the fixed substance and the carrier, so that, for example, a fixed enzyme on a hydrated substrate consisting of a polysaccharide finds itself in a quasi-natural environment. Because of their relatively well-defined nature, cross-linked dextrans, such as are obtained, for example, from the reaction of dextran with epichlorohydrin (compare Swiss Pat. No. 501,695) are preferentially used as carriers. Because of their high swellability, the same patent also recommends correspondingly cross-linked starch gels and agarose as well as mercerised cellulose.

In order to fix the peptide substances, the said carrier materials must be "activated" by the introduction of functional groups, so that at least one chemical bond to the carrier is produced per peptide molecule by chemical reaction between carrier-bound functional groups and the peptide substance. Again, there are numerous proposals [references are given, inter alia, in Axen et al., Nature (1967) 214, 1302]. As a particularly mild method, the same literature reference and the Swiss Patent already mentioned (No. 501,695) propose activation of a polymer containing hydroxyl groups or amino groups by means of a cyanogen halide. This process has since then found wide acceptance in spite of its relatively expensive starting product (pre-cross-linked polymer on the one hand and cyanogen bromide on the other) and in spite of the unpleasant properties of the cyanogen halides.

With regard to the chemical reaction which occurs during the activation process, the nature of the active functional groups and its mode of reaction with the peptide substance, the only thing reliably known is that the activation takes place at the hydroxyl groups of the carrier and the fixing takes place via basic nitrogen of the peptide substance.

Given this situation, there appeared to be no prospect of discovering a process which was equivalent in respect of product quality, less demanding in respect of the starting products and simpler in respect of the technical effort required, that is to say a process which, viewed overall, was of equivalent utility but economically superior. On the other hand, the requirement for such a process is probably undisputed since the manufacture and use of fixed enzymes, particularly in biotechnology, is, in the present-day state of the art, above all a question of what is possible with regard to costs.

It has now been found, surprisingly, that it is nevertheless possible to arrive, by a short, inexpensive and very simple route, at carriers which are able to fix amines, and at carrier-fixed amino compounds which are qualitatively and quantitatively of high standard and are biologically active where relevant. This can be accomplished with the use of hydrocyanic acid and/or a watersoluble cyanide and a reagent which contains positive chlorine or bromine, namely hypochlorous acid or hypobromous acid and/or a water-soluble salt of hypochlorous acid or hypobromous acid or a chlorine compound or bromine compound which on hydrolysis yields one of the acids mentioned, or a mixture of such halogen derivatives. Such materials are allowed to act on a water-soluble or swellable waterinsoluble polyhydroxy compound in an alkaline medium, preferably in the cold, the reaction mixture is optionally neutralised and (a) in the case of a solution is freed of low molecular constituents by clarification and dialysis or gel filtration, (b) in the case of a suspension is freed of low molecular constituents by filtration or centrifuging and elution. The cross-linking and activation product present in solution or suspension or remaining as a filter residue or centrifuge residue is allowed to act, in the presence of water and optionally a buffer system, at a temperature below 50°C, preferably in the cold, on an optionally biologically active, water-soluble amino compound which is capable of substitution on at least one basic nitrogen atom, and dialysable material or material which has remained in a dissolved form is dialysed or filtered or washed out of the reaction product by means of water or an aqueous salt solution.

A suitable water-soluble cyanide is, in particular, an alkali metal cyanide, for example sodium cyanide or potassium cyanide. The total cyanide, that is to say the sum of hydrocyanic acid and water-soluble cyanide, is advantageously employed in an amount which ranges, without a sharp limit, from 0.25 to 6 gram equivalent per gram equivalent of polymer-bound hydroxyl.

It is possible initially to take the total cyanide together with the polyhydroxy compound and to add the reagent which contains positive chlorine and bromine and is hereafter for brevity referred to as 37 reagent". The degree of cross-linking and amine fixing capacity then depend on the amount of the "reagent", as long as the latter remains present in less than equivalent amount compared to the total cyanide. Further factors are the "hydroxyl group density" on the polyhydroxy compound catalyst, and the molecular weight and reactivity of this compound.

If the amount of "reagent" consumed per gram equivalent of organically bound hydroxyl is greater than ¼ or ½ gram-mol, remaining excess total cyanide has no significant influence on the cross-linking reaction and activation reaction. It is however more appropriate largely or wholly to utilise the total cyanide taken initially by adding only slightly less than the equivalent amount, or the theoretical amount, of "reagent". In the latter case, exceeding the equivalence point is frequently recognisable, for example when working with hypochlorite, from a blue colouration of potassium iodide/starch paper by the alkaline reaction solution. It is desirable only to approach the equivalence point where the cross-linking reaction has largely taken place. At an earlier stage, excess "reagent" can prematurely stop the cross-linking reaction and the activation. After completion of the cross-linking and activation, an excess of "reagent" is admittedly superfluous, but also harmless as long as it does not significantly exceed 100%. Otherwise, the cyanate formed in a side reaction may no longer suffice to protect the cross-linked and activated polymer against damage, for example by hypochlorite; this is because cyanate reduces hypochlorite according to the equation:

$$2 NCO^- + 3 OCl^- + H_2O \rightarrow 2HCO_3^- + 3 Cl^- + N_2$$

[Lister, Can. J. Chem. 33, 426 – 440 (1955)].
The quantities indicated above circumscribe the practical working range but represent neither an upper nor a lower limit.

An embodiment related to that described above consists of initially taking only a part of the total cyanide together with the polyhydroxy compound and to introduce the remainder conjointly with the "reagent" into the reaction mixture. Here it is desirable to ensure that at least up to completion of the addition the cyanide is present in excess in the reaction mixture.

It is however also possible first to take the "reagent" and to add the mixture of total cyanide and polyhydroxy compound. In that case it is inappropriate to use an excess of "reagent" since otherwise the cyanide is "trapped".

The addition of "reagent", especially hypochlorite, to the polyhydroxy compound can also take place before addition of the cyanide. In that case an appropriate method is to add the aqueous mixture of, for example, hypochlorite and polyhydroxy compound dropwise to the aqueous cyanide solution while stirring and cooling efficiently, at about 0°C. As described below, it is under certain conditions also possible to add the cyanide solution all at once to the mixture of, for example, hypochlorite and polyhydroxy compound. The considerable amount of heat involved in the latter case demands particularly efficient cooling.

"Reagent", especially hypochlorite, and polyhydroxy compound appear, as described in more detail below, to act on one another in that a part of the hydroxyl groups are esterified by hypochlorous acid. This reaction can optionally be favoured by introduction of $CO_2$ or addition of solid carbon dioxide. When using such pre-treated mixtures, especially of hypochlorite and polyhydroxy compound, it is however necessary to take care, where appropriate, that the alkalinity of the cyanide solution suffices to balance the $CO_2$-conditioned looss of alkalinity in the "reagent" solution.

Hypochlorite in the form of sodium hypochlorite bleach or potassium hypochlorite bleach is a preferred form of the "reagent".

Instead of hypochlorite it is also possible to use a mixture of alkali metal hydroxide solution or alkali metal carbonate solution and gaseous chlorine, it being possible to introduce the alkali initially with the polyhydroxy compound and the cyanide or only to add it gradually to the reaction mixture during the introduction of the chlorine. Here again the sequence can be reversed by first adding chlorine, and only then the cyanide, to the hydroxy compound and the alkali. As regards the stoichiometry, the same applies as when using hypochlorite apply. As in the case of the preparation of hypochlorite solution, a slight excess of alkali relative to chlorine is recommended.

In general, the alkali metal hypochlorite in the process according to the invention can be replaced by compounds which on hydrolysis form hypochlorous acid. These include [Houben-Weyl 5/3 (1962), page 760] the esters of hypochlorous acid and nitrogen compounds of which the chlorine is bonded to nitrogen such as, for example, chlorimides, chloramides, chlorimines and chloramines. There may be mentioned ethyl hypochlorite, propyl hypochlorite and tert.-butyl hypochlorite (Houben-Weyl 5/3, 765 and 6/3, 491, 492), N-chloro-succinimide (Houben-Weyl 5/3, 800), N-chloroacetamide (Houben-Weyl 5/3, 799), Chloramine T and Dichloramine T (Houben-Weyl 5/3, 808) as well as chloramine (Houben-Weyl 5/3, 796).

A statement according to which chloramine with potassium cyanide gives cyanogen chloride (Beilstein 3 E II, 32) has proved to be incorrect: cyanogen chloride is not produced, but considerable amounts of potassium cyanate are produced [Markwald and Wille, Ber. dtsch. chem. Ges. 56, 1325 (1923)].

Like N-chlorine compounds, analogous bromine compounds, such as, for example, N-bromosuccinimide or N-bromocetamide, have proved to be capable of very successful use. For this reason, the new process also includes the use of the corresponding N-bromo compounds and not least the use of the alakli metal hypobromites and of hypobromous acid itself.

Appropriately, the choice of the N-halogenated compound with a basic nitrogen group is restricted to products which when donating halogen liberate, directly or after mild hydrolysis, either ammonia or a tertiary amine. Examples are chloramine ($NH_2Cl$) and pyridinium bromide perbromide [Bull. Soc. Chim. France 1952, 331]. Experience has shown that ammonia leaves the amine-fixing groups intact because its action is presumably restricted to a replacement reaction; tertiary bases are not fixed, because of the absence of hydrogen which can be replaced. The lower aliphatic alcohols from the hypochlorites as a rule only complete insignificantly with the polyhydroxy compounds during the O-cyanation.

Cross-linking and activation require an alkaline reaction medium, preferably in the range of about pH 10 to about pH 13. This pH becomes established automatically if, for example, one of the solutions, described below, of sodium hypochlorite (sodium hypochlorite bleach) or chloramine or Chloramine T or t-butyl hypochlorite in bulk form is added to the aqueous mixture of polyhydroxy compound and sodium cyanide. This is also true if first an aqueous mixture of polyhydroxy compound and one of the halogen carriers just mentioned is prepared and the mixture is added to the aqueous solution of sodium cyanide. In other cases, where the initially taken component, or the component to be introduced, of the reaction mixture is too alkaline, insufficiently alkaline or even acid, and the other component possesses insufficient buffering capacity to ensure that the mixture of the components has the desired pH, strong or weak acid, strong or weak base or a buffer salt, such as, say, hypochloric acid or carbon dioxide, alkali metal hydroxide or ammonia, alkali metal carbonate or alkali metal bicarbonate or ammonium chloride is added to one or both components. An example is provided in the use of chlorine water as a source of positive chlorine and another example in the use of hydrocyanic acid as a source for cyanide. Appropriate buffering measures will of course also be taken when both components are too alkaline, insufficiently alkaline or acid.

By a component of the reaction mixture there is generally understood (1) the mixture of the polyhydroxy compound with cyanide and/or hydrocyanic acid or (2) the mixture of the polyhydroxy compound with the "reagent". The other, supplementary component is then the agent still required for the reaction according to the invention, namely the "reagent", or cyanide and/or hydrocyanic acid. Each of the components thus defined can, for the purpose of carrying out the reaction, either be taken initially, with the missing counter-component then being added, or vice versa.

It should be noted that at the lower limit of the indicated pH range both hydrocyanic acid, and hypochlorous and hypobromous acid are incompletely neutralised.

It can thus be advantageous, according to the above, to wholly or partially neutralise hypochlorous acid or hypobromous acid which is produced by hydrolytic decomposition of organic hypochlorites or nitrogen compounds which contain positive chlorine or bromine. If the nitrogen compound in question is itself basic in character, the neutralisation loses its significance. The alkalising function of alkali metal hydroxides and alkali metal carbonates can also be taken over by excess alkali metal cyanide. If the N-halogen compound is already in the form of a salt, as in the case of Chloramine T of the formula $CH_3C_6H_4SO_2NNaCl$, the neutralisation of the hypohalous acid has been taken care of and additional alkali tends to be harmful.

Suitable polyhydroxy compounds are above all carbohydrates such as starch, starch, paste, soluble starch, dextrins, dextrans, cross-linked dextrans, cellulose, especially mercerised cellulose, cellulose fibres, agarose, pectins and the like.

The degree of polymerisation of the polyhydroxy compounds from the class of the carbohydrates which can be used as starting materials is optional, provided these compounds have the requisite solubility or swellability. Even saccharose gives, according to the invention, an insoluble product having a very good enzyme fixing capacity. However, it is not essential to use carbohydrates. Water-soluble polyvinyl alcohols are also cross-linked, for example in the system cyanide/hypochlorite, to give insoluble hydrophilic products of satisfactory amine fixing capacity.

The cross-linking and activation of the polyhydroxy compound take place in the temperature range between the solidification point of the solution and about 50°C; appropriately, they are carried out at between 0°C and room temperature.

Thus, in treating the said polyhydroxy compounds with "reagent" and cyanide, the following takes place according to the invention:

If the polyhydroxy compound employed is watersoluble and dialysable such as, for example, sucrose (cane sugar), or if it is only water-Soluble, such as soluble starch, dextrins and dextrans, they yield, within a very short time, a polycondensate, in practically quantitative yield, which precipitates in thick flocks. Substances of higher molecular weight, such as starch paste, lose their gel-like nature and become flocculent and filterable. Cross-linked dextrans, which are insoluble, undergo densification of their structure. Less distinct but nevertheless detectable changes are to be found in the case of mercerised cellulose and agarose. All these substances are distinguished by a pronounced capacity for amine fixing; they are fixing-active.

The combination of cross-linking and activation, which permits the use of even the cheapest polyhydroxy compounds, and which yields, in a single step, a high quality activated cross-linking product and requires, for this, merely the use of the commonest of chemicals and apparatuses, is to be regarded as a considerable, unexpected and economically important technical advance. The activated product is outstandingly suitable for fixing proteins, polypeptides, oligopeptides, aminoacids or amines of the general formula:

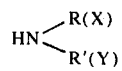

wherein R(X) denotes hydrogen or a radical with hydrogen or with a functional group in position X and R'(Y) denotes a radical with hydrogen or a functional group in position Y. This thus opens up a very simple method for obtaining polysaccharides having functional additional groups of optional nature, provided they are stable to water.

If the activated products are water-insoluble, they can remain in suspension and can, after the alkali has been neutralised, be reacted further directly with the amino compound. However, in some cases it is more advantageous to collect the insoluble material on a filter and to elute it, for which water, salt solutions and buffers, with or without addition of protein stabilisers (for example glycerine or complex-forming agents) can be used, and then to react the moist filter residue, again without delay because of the limited life of the active functional groups, with a water-soluble amino compound.

If they are water-soluble, the activated products can, if appropriate after neutralisation of the alkali, be reacted further directly with the amino compound. However, in some cases it is more advantageous to remove low molecular material, if appropriate after neutralising the alkali, by dialysis and only then to carry out the reaction with the amino compound.

The insoluble fixing products possess excellent filterability and because of their hydrodynamic properties are also very suitable for use in flowing reaction systems (continuous column operation).

Soluble but not dialysable fixing products can be obtained when reacting low molecular amino compounds with activated cross-linking products from, for example, soluble starch, which are only slightly cross-linked and therefore do not flocculate, or with activated pectins and mucins which, in spite of cross-linking, remain in solution.

The reaction between the cyanide/"reagent"-cross-linked and -activated polyhydroxy compound and the amino compound is preferably carried out in a neutral to weakly alkaline or moderately alkaline range, for example in the presence of water or sodium bicarbonate or sodium carbonate. It has proved advantageous to employ an excess of the amino compound and to carry out the reaction in the cold if necessary, and it is desirable to use as high a concentration as possible. In the case of a filter residue, the water present therein frequently suffices to dissolve dry amino compounds which are in lyophilised form. For this purpose, the amino compound is simply stirred into the filter residue. On leaving the mixture to stand, fixing takes place; it can be accelerated by occasionally turning over the filter residue.

The following were fixed, in aqueous alkali metal bicarbonate solution, to the water-soluble polymers described above: oxytocin, vasopressin, angiotensin and $\beta^{1-24}$-corticotropin. After the reaction has taken place, the mixture is filtered (Sephadex G-25) or dialysed to remove unreacted material and salts. According to aminoacid analysis the products contain between 2 and 20% of peptide material per gram of dry substance.

In the case of the water-insoluble polymers described above, the following enzymes were introduced into the filter residue by stirring, and fixed, in the presence of sodium bicarbonate which originated from the wash liquor of the filter residue (1 percent strength NaHCO$_3$ solution) and, in a second series of experiments, in the additional presence of glycerine which also originated from the washing process (last wash liquor: 10 percent strength glycerine, 1 percent strength NaHCO$_3$): hexokinase, ribonuclease, trypsin, chymotrypsin, carboxypeptidase and acyl-L-amino-acid-acylase.

Advantageously ¼ to ½ and optionally a whole part by weight of protein is employed per 1 part (dry weight) of activated carrier. The proportion of protein in the carrier-protein compounds is about 3 to 30% of the dry weight (aminoacid analysis).

All activation stages based on 50 to 400 mg of sodium cyanide per 100 mg (dry weight) of "amylopectin fraction", starch, water-soluble starch, dextrin, dextran, cellulose, cellulose fibres, Sephadex G 200, sucrose and polyvinyl alcohol yield enzymatically active material which possesses a stability which is characteristic of the carbohydrate-fixed preparations.

While the enzymes are as a rule best added in dry form to the filter cake, it frequently proves advantageous to employ low molecular amino compounds such as oligopeptides, aliphatic and aromatic aminocarboxylic acids and aminosulphonic acids, aminophenols, aliphatic and aromatic aminoalcohols, diamines and polyamines, as well as aliphatic, alicyclic and heterocyclic amines and water-soluble derivatives of all these substances, which still contain basic nitrogen capable of substitution, in the form of more or less concentrated aqueous solutions for the fixing reaction.

Thus, for example, the following amino compounds were fixed successfully from aqueous solution to an "amylopeptin fraction" treated with cyanide/hypochlorite: the sequence peptide Gly-Pro-Ala-Gly-Pro-Ala for carrying out degradation reactions in a heterogeneous medium; the S-peptide from ribonuclease for use in affinity chromatography; p-aminophenyl-α-N-acetyl-alanine as a substrate of an analogue of an acylaminoacid acylase; glycyl-phenylalanine as a substrate of an analogue of the same acylaminoacid acylase; glutamic acid and sulphanilic acid for obtaining chromatographic adsorbents; dehydroabietylamine for obtaining an optically active salt-forming agent; imidazole for obtaining a hydrolysis catalyst; hydroxylamine, hydrazine, phenylhydrazine, p-aminophenol and p-phenylenediamine for obtaining reducing agents.

The properties of the fixed amino compounds, in particular the properties of fixed biologically active peptides and proteins, vary within the limits of relevant data in the literature and patent literature.

The questions of what are the chemical reactions on which the cross-linking of the polyhydroxy compounds is based, and on what the activity, that is to say the ability of the cross-linked product to fix amino compounds, is based, have not been elucidated. The hypothesis of an intermediate formation of cyanogen chloride could be excluded experimentally in that under comparable conditions cyanide/hypochlorite reacted distinctly differently from cyanogen chloride.

It is admittedly known that chlorine produces cyanogen chloride from an alkali metal cyanide at below pH 9, cyanogen chloride is converted into alkali metal cyanate by means of alkali metal hydroxide solution and during the hypochlorite oxidation of alkali metal cyanide to alkali metal cyanate an odour reminiscent of cyanogen chloride is observed. For this reason the view — though not uncontested — is found in the literature that the practically instantaneous formation of cyanate in the oxidation of cyanide by means of hypochlorite takes place via cyanogen chloride.

Nevertheless the treatment, according to the invention, of polyhydroxy compounds with hypohalite/cyanide (hereafter referred to as II) is not a variant of the known alkali/cyanogen halide treatment of polyhydroxy compounds (hereafter referred to as I). This can be demonstrated particularly simply and convincingly if water-soluble polyhydroxy compounds, for example water-soluble starch, are employed in I and II. Under suitable conditions, the soluble starch becomes insoluble, both after I and after II, as a result of cross-linking. The cross-linking products precipitate in a flocculent form, can easily be isolated and possess the known amine fixing capacity of products such as are obtained, for example, according to Swiss Pat. No. 501,695 by cyanogen halide activation of cross-linked dextran (Sephadex) or cellulose.

The cross-linking of starch and the evidently simultaneous introduction of amine fixing capacity can, according to views discussed at the present time, be formulated schematically somewhat as follows:

Scheme

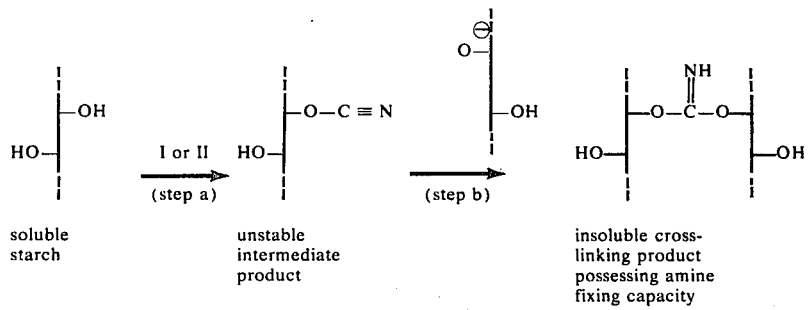

soluble starch     unstable intermediate product     insoluble cross-linking product possessing amine fixing capacity According to this, the cross-linking reaction (steb b) would be identical for I and II, and would thus have the same pH dependence. The O-cyanation (step a) is, in the case of I, dependent on the presence of deprotonised hydroxyl groups of the starch and is subject to competition by hydroxyl ions from the alkaline medium (formation of alkali metal cyanate as a by-product). In the case of II, the circumstances would have to be the same if the first step in the course of II were actually to consist of an instantaneous [compare Gmelins Handbuch der Anorganischen Chemie (Gmelins Handbook of Inorganic Chemistry), 8th edition, C [D 1 ] 14, pages 35 and 37 (1971)] formation of cyanogen halide; above all, under comparable conditions I would always have to be at least as fast as II. However, if the hypothesis that II takes place via cyanogen halide is abandoned, it becomes possible — where step a becomes the rate-determining step for the overall reaction (separation of an insoluble cross-linking product) — for II to have a different pH-dependence than that of I. This is exactly what is found experimentally, as will be described in more detail in the appendix.

The examples of the cross-linking and activation reaction and of the amine fixing which follow are not intended in any way to restrict the scope of the invention. The temperature is given in °C throughout.

EXPERIMENTAL SECTION

I. The cross-linking and activation reaction

Reagents: Sodium hypochlorite bleach. The preparations used are those obtained when treating 80 g of NaOH, 375 g of water and 375 g of ice below 0°C with gaseous chlorine, while stirring vigorously, until a weight increase of 66 g is reached (5 hours). Such freshly prepared solutions contain approximately 7.5 per cent by weight of sodium hypochlorite (iodometric analysis); the pH-value is about 11.5.

Sodium cyanide. Commercial material of "practical" grade was found to have almost 100% strength on titration with sodium hypochlorite bleach.

Polyhydroxy compounds: water-soluble starch, potato starch, water-soluble polyvinyl alcohol, sugar (sucrose), Avicel cellulose powder (mercerised), powdered fibrous cellulose MN 300 (Messrs. Macherey and Nagel), cotton yarn (mercerised) and viscose rayon (mercerised) were commercial preparations. Experimental method: see the individual examples below. working up: soluble cross-linking products were prepurified by filtering or centrifuging (clarifying) their solution and were freed of low molecular substances by dialysis or gel filtration. Insoluble cross-linking products were as a rule obtained in a flocculent form, could in general be filtered easily, and were then as far as possible freed immediately of alkali and other soluble substances by filtration and elution with water. If they were not used immediately for amine fixing, they were preferably stored in the cold. On the other hand, the amine fixing capacity is astonishingly stable. Standing for several days in the moist state at room temperature proved permissible in very many cases.

EXAMPLES

1. Water-soluble starch/hypochlorite or hypochlorous acid 2 g of water-soluble starch are suspended in 100 ml of water, and the mixture is heated on a waterbath until dissolved and is allowed to cool. To 5 ml portions of this starch solution (each containing 100 mg of starch, corresponding to about 2 milliequivalents of —OH) were added, in each case, 100 mg (2 mmols) of sodium cyanide, diluted to 10,25 or 50 ml with water, the mixture was cooled to −5° or 0° or 10°C and bleach corresponding to an amount of ½ or 1 or 2 or 4 mmols of sodium hypochlorite was added dropwise with good cooling. Flocculation commences after addition of 0.5 to 1 mmol of sodium hypochlorite, largely independently of the temperature and volume of the reaction mixture. The dry weight of the precipitates is about 100 mg. The same series of experiments with only 50 mg (1 mmol) of sodium cyanide gives approximately the same result.

If these experiments are carried out by adding the entire amount of hypochlorite at once to the starch/cyanide mixture, flocculation only takes place reliably if the cyanide was present in excess. If a less than equivalent amount of cyanide was present, the reaction appears essentially to be restricted to the oxidation of the cyanide.

This latter impression is confirmed if the hypochlorite is taken first and the starch/cyanide mixture is added thereto. If this addition is made dropwise, no product flocculation occurs even if there is an excess of cyanide. If, on the other hand, the addition is made all at once, product flocculation can be observed in the case of an excess of cyanide. Compare, in this context, the discussion of the reaction mechanism given in the appendix.

The pH-value of the above reaction solutions is about 12. If the starch/cyanide mixture is diluted with 0.1 N sodium hydroxide solution instead of water, no product flocculation takes place. A pH of 13 thus approximately represents the upper limit. If 100 mg of starch and 100 mg of sodium cyanide are first introduced into 15 ml of water (pH 11.2) and 2 mmols of sodium hypochlorite and 2 mmols of sodium bicarbonate in 10 ml of water (pH 10.8), or the reaction product of 2 mmols of sodium hypochlorite and 1 g of solid $CO_2$ in 10 ml of water (pH 7.8) are then added over the course of 5 minutes at 0° – 5°C, flocculation in both cases occurs even before the addition is complete; after completion of the addition, the pH-values are about 11.0 and 10.6.

If on the other hand 2 mmols of HCl and 2.5 mmols of $K_2CO_3$ (total volume 15 ml, pH 10.0) are added to the same starch/cyanide mixture, the above solution of hypochlorous acid of pH 7.8 no longer causes product flocculation in every case. The final pH-value of such reaction mixtures is about 10.0. No flocculation occurs if the starch/cyanide mixture has a pH of 9.8 because of addition of 2 mmols of HCl and 0.1 mmol of $K_2CO_3$ or a pH of approximately 7 because of addition of 2 mmols of HCl and the pH, after reaction with the solution of hypochlorous acid of pH 7.8, is about 9.6 or 7.5. This shows that the lower pH limit has a value of about 10. The alkalinity of starch/cyanide mixture can optionally also be buffered by addition of ammonium chloride.

2. Water-soluble starch/chlorine and sodium hydroxide solution or potassium carbonate 100 mg (2 mmols) of sodium cyanide, 2 ml or more of a 1 M solution of potassium carbonate (at least 2 mmols) and 8 ml of water are added to 5 ml of a starch solution (100 mg of starch), the mixture is cooled to 0°C, 10 g of ice are added and chlorine gas (2 mmols) is passed in, while cooling well, until the reaction mixture gives a positive reaction with potassium iodide/starch paper. The product precipitates in a flocculent form. This is also the case if 5 ml of starch solution, 2 ml of 2 N sodium hydroxide solution, 3 ml of water and 10 g of ice are treated with chlorine (approx. 2 mmols), while cooling, until the pH-value is between 9.5 and 10, and a solution of at least 100 mg of sodium cyanide in 5 ml of water is then poured on top of the mixture, all at once. It should be noted that in this embodiment an excess of cyanide is necessary.

3. Starch paste/bromine and sodium hydroxide solution or potassium bicarbonate 300 mg of starch in 35 ml of water are warmed to 70°C, allowed to cool and centrifuged for 5 minutes at 3,000 revolutions per minute, the supernatant liquor is decanted, 2 ml of 2 N sodium hydroxide solution and 0.5 ml of a solution of 110 mg (2.2 mmols) of sodium cyanide in 5 ml of water are added to the residue, which has a dry weight of about 100 mg, the mixture is cooled to 0° – 5°C and the remaining cyanide solution and 320 mg of bromine (2 mmols) are now added simultaneously but separately with vigorous stirring, in such a way that at no point can excess bromine or hypobromite be detected with potassium iodide/starch paper. A cross-linking product of good filtrability flocculates. The result is approximately the same when using twice the amount of sodium hydroxide solution, cyanide and bromine, but is not as good when using half the amount in each case.

It is also possible to add 110 mg of sodium cyanide (2.2 mmols), at least 4 ml of a 1 M solution of potassium bicarbonate and then — dropwise and with cooling — 320 mg of bromine (2 mmols) to the starch paste, after which the paste becomes filterable as a result of modification by cross-linking.

In a third variant, 320 mg of bromine are added to the starch paste, at least 4 ml of 1 M potassium bicarbonate solution are added dropwise while stirring well and cooling, the mixture is left to stand for 15 minutes and a solution of 140 mg of sodium cyanide (2.8 mmols) in 5 ml of water is added all at once, while ensuring very thorough stirring.

4. Water-soluble starch/chloramine T 100 mg (2 mmols) of sodium cyanide in 20 ml of water are added to 5 ml of starch solution (100 mg of starch) and a solution of 562 mg (2 mmols) of the trihydrate of chloramine T in 2 ml of dioxane is added dropwise over the course of 11 minutes at 5°C, while stirring well. The product flocculates even before the end of the addition of the chloramine. The same success is achieved if the reaction is carried out at 20°C and/or an aqueous solution of chloramine T is used.

5. Water-soluble starch/N-bromosuccinimide 100 mg (2 mmols) of sodium cyanide in 15 ml of water and 1 ml of 2 N sodium hydroxide solution are added to 5 ml of starch solution (100 mg of starch), and thereafter a solution of 360 mg of bromosuccinimide in 2 ml of dioxane is added dropwise at 20°C, while stirring. Duration approx. 15 minutes. The reaction already manifests itself after about 7 minutes through appearance of turbidity.

Instead of N-bromosuccinimide, N-bromoacetamide or N-chlorosuccinimide can also be used.

6. Water-soluble starch/chloramine

Sodium hypochlorite bleach (1 mol of sodium hypochlorite per mol of ammonia) is added to a mixture of 1 N ammonia and ice, the mixture is distilled in vacuo (boiling point$_{20}$ = 35°C) and the aqueous chloramine solution is condensed in a well-cooled receiver. Its strength is determined iodometrically. 5 ml of starch solution (100 mg of starch) are treated with 100 mg (2 mmols) of sodium cyanide in 10 ml of water, the mixture is cooled to 2° – 4°C and 10 ml of chloramine solution (2 mmols) are added dropwise while stirring well, and cooling. A cross-linking product of very good filterability precipitates; dry weight approx. 100 mg. A little ammonia in the chloramine solution does no harm.

7. Water-soluble starch/t-butyl hypochlorite 217 mg (2 mmols) of freshly prepared but not distilled t-butyl hypochlorite are added dropwise to 5 ml of starch solution (100 mg of starch) and 100 mg of sodium cyanide (2 mmols) in 20 ml of water (pH 11.1) at 5°C, while stirring well. Even before the yellow drops of ester have completely disappeared the reaction commences (opalescence), and some seconds later the cross-linked reaction product flocculates (pH 10.8). A similar result is obtained if 1 or 2 ml of a 1 M solution of potassium carbonate is added beforehand to the starch/cyanide mixture.

The esters of hypochlorous acid with ethanol, propanol or tert. amyl alcohol are used with equal success.

8. Water-soluble products with amine fixing capacity

By using higher dilutions (50 ml, 100 ml or more per 100 mg of water-soluble starch), conditions are achieved, in accordance with the processes described under 1 – 2 Examples and 4 – 7, in the prescribed pH range, and especially with vigorous stirring, under which flocculation no longer occurs but the dissolved substance can nevertheless be demonstrated to possess an amine fixing capacity, especially towards low molecular dialysable amino compounds. A qualitatively identical effect is achieved by reducing the amount of cyanide or hypochlorite which limits the cross-linking to about 0.25 equivalent per equivalent of organic hydroxyl.

9. Sucrose/hypochlorite 100 mg of sucrose (sugar) are dissolved in 10 ml of water (2.34 milligram equivalents of organic hydroxyl), 100 mg of sodium cyanide (2 mmols) are added, the mixture is cooled to 5° – 10°C and 2 mmols of sodium hypochlorite in the form of sodium hypochlorite bleach are added while stirring vigorously. After addition of half the amount of hypochlorite a flocculent cross-linking product already precipitates. It is filtered off after completion of the addition of hypochlorite and thoroughly eluted. Its amine fixing capacity is perfect; the dry weight is about 100 mg. It is noteworthy that on standing in an alkaline reaction medium this compound liquefies after a few hours. A product which is obtained from 100 mg of sucrose, 10 mg of water and 106 (1 mmol) or 212 (2 mmols) of cyanogen bromide and 1 or 2 ml of 1 N NaOH possesses the same property. These sucrose derivatives are new.

Other non-reducing oligosaccharides, for example the trisaccharide raffinose and the tetrasaccharide stachyose behave analagously. Their cross-linking products are also new compounds.

10. Polyvinyl alcohol/hypochlorite 100 mg of polyvinyl alcohol (2.3 milligram equivalents of organic hydroxyl) are dissolved in 10 ml of boiling water, 100 mg (2 mmols) of sodium cyanide are added to the cooled solution and 2 mmols of sodium hypochlorite in the form of sodium hypochlorite bleach are then added at 0° – 5°C while stirring. The cross-linking product precipitates in coarse somewhat smeary flocks but can nevertheless be filtered off and washed. The product is stable in contact with water, like the products from Examples 1 to 9, but liquefies, like the sucrose derivative, on standing in an alkaline reaction medium.

11. Cotton yarn/hypochlorite or hypochlorous acid 500 mg of crude cotton yarn are boiled with water and degreased by washing twice with alcohol, twice with carbon tetrachloride and twice with ether, and dried in air. The yarn is subsequently left to stand overnight in 17% strength sodium hydroxide solution with exclusion of air, and is washed thoroughly and treated with 500 mg of sodium cyanide in 10 ml of water and subsequently, at 0° – 5°C, with 10 mmols of sodium hypochlorite, in the form of sodium hypochlorite bleach, added dropwise. The yarn is washed thoroughly and the amine binding capacity is determined by enzyme fixing and then carrying out several successive activity tests, the material being thoroughly washed afresh between each test. This precautionary measure is necessary because non-specific enzyme fixing on mercerised fibres has also been observed and because the acid sensitivity of the enzyme preparation excludes the otherwise customary process of washing with a weakly acid buffer.

A variant consists of treating the washed and mercerised yarn with the above-mentioned amount of sodium hydroxide bleach and excess solid $CO_2$, to decant the liquid and to introduce the yarn into the aqueous solution of 500 mg of sodium cyanide. After standing for 5 – 10 minutes, the solution is decanted and the yarn is washed with water.

In a third variant, the washed and mercerised yarn (500 mg) is incubated with 3 g of sodium cyanide in as little water as possible overnight and after dilution with 25 ml of water 60 mmols of sodium hypochlorite are added with intense cooling, vigorous stirring being necessary.

12. Viscose yarn/hypochlorite 250 mg of viscose yarn are suspended in 2 N sodium hydroxide solution, the solution is decanted after 1 hour, the yarn is washed with water and covered with a solution of 500 mg of sodium cyanide in 5 ml of water, the mixture is incubated for 30 minutes and cooled to 5°C, and 10 mmols of sodium hypochlorite in the form of 7 per cent strength sodium hypochlorite bleach are added over the course of 30 minutes with vigorous stirring; the yarn is then thoroughly washed with water.

13. Instead of the water-soluble starch, it is possible to use, according to Examples 1–2 and 4–8, dextrins or mixtures of dextrins and water-soluble starch or mixtures of water-soluble starch and polyvinyl alcohol. Equally, sodium hypochlorite bleach can be replaced by an equivalent amount of potassium hypochlorite bleach and sodium cyanide can be replaced by potassium cyanide; the bleach solutions used were titrated in each case.

14. Working temperatures of 25° to 50°C are used in order to avoid gelling of the educt and of the product when using concentrated solutions. An example is the application of the process to the cross-linking and activation of pectins and of mucins which remain water-soluble under moderate cross-linking.

14a. "Amylopectin fraction"/hypochlorite 1 gram of potato starch is suspended in 1 liter of water. The mixture is warmed to 70°C while stirring, kept for one hour at this temperature and allowed to cool, and the fraction which is highly swollen but has remained insoluble is separated off by centrifuging. After repeating the warm water treatment and again separating the product on the centrifuge, an "amylopectin" fraction with a dry weight which is about one-third of that of the starch employed remains; see Advances in Carbohydrate Chemistry, Vol. 1, page 262, Academic Press Inc. Publishers, New York 1945.

Approx. 100 mg each (dry weight) of soaked starch and "amylopectin fraction" are suspended in 35 ml of water, 25 or 50 or 100 or 200 or 400 mg of sodium cyanide are added and subsequently — using ice-cooling in one series of experiments and working at room temperature in a second series of experiments — 3 per cent (weight/weight) Javelle solution is added dropwise, with vigorous stirring, until the KI-starch test just showed that an excess of hypochlorite persisted. Hypochlorite consumption: 1 mol per mol of sodium cyanide. The pH-value rises from about 10.5 (cyanide solution) to about 12. Duration of the experiment 5 – 20 minutes. Results with regard to cross-linking: starch shows good filterability from 25 mg of cyanide onwards; "amylopectin fraction" becomes flocculent and possesses very good filterability from 50 mg of cyanide onwards.

The result remains practically the same if 6 per cent (weight/weight) Javelle solution is used.

The result of an "amylopectin fraction" batch with 50 mg of cyanide also does not change if the 6 per cent strength Javelle solution is adjusted to pH 6 before use: here again the pH-value rises from initially 10.5 progressively towards 11 and the product is perfect with regard to flocculation, filterability and degree of activation. If, on the other hand, the pH is adjusted to 6 or 8 after addition of the cyanide and the hypochlorite is then added at the same pH (pH-stat), there is no flocculation whatsoever; the hypochlorite consumption per mol of cyanide increases in all these cases, presumably because of partial disproportionation of the hypochlorite with formation of chlorate and sodium chloride, or because of oxidation to cyanate.

14b. Cellulose/Hypochlorite 300 mg of microcrystalline cellulose powder (AVICEL) and 100 mg of powdered fibrous cellulose MN 300 (Messrs. Macherey and Nagel) are suspended in water for 2 hours. A third sample, again of fibre cellulose MN 300, is mercerised overnight in 17.5 per cent strength sodium hydroxide solution, with exclusion of air. Thereafter, the three samples are each activated with 50 mg of sodium cyanide and Javelle solution as described under I. In each case, the cellulose became more granular and denser; it can be filtered readily.

The hypochlorite consumption is here again 1 mol per mol of cyanide. The presence of the mercerising liquor interferes with the course of the reaction because of the increased alkalinity. Therefore, it is advisable first to remove or neutralise the sodium hydroxide solution.

14c. Sephadex G 200/hypochlorite 100 mg portions of Sephadex G 200 (Pharmacia Fine Chemicals AB, Uppsala) are activated, as described under 14a, with amounts of 25 to 400 mg of sodium cyanide and Javelle solution, the hypochlorite consumption and pH change lying within the indicated limits. The Sephadex also becomes denser so that it can now be used, for example, as a column packing in rapid liquid chromatography.

15. Potato starch/hypochlorite 10 g of edible grade potato starch are suspended in 1 l of water, the suspension is warmed to 60°C for one hour while stirring gently and is centrifuged, the supernatant liquid is decanted, the residue, which has a volume of about 450 ml, is treated with 14.7 g (0.3 mol) of sodium cyanide, stirred and cooled to 10°C, and 130 ml (0.25 mol of hypochlorite) of sodium hypochlorite bleach are allowed to run in over the course of 30 minutes. The pH-value rises from 11 to 12.5. The product is filtered off on a glass frit and washed with 1.5 l of ice water. The product is used immediately or is stored in the frozen or lyophilised state.

In variant A, 10 g of starch of the same quality are suspended in 500 ml of water, the mixture is heated to 60°C for 30 minutes and is allowed to cool, 24.5 g (0.5 mol) of sodium cyanide are added, the whole is cooled to 5°C, and 200 ml (0.38 mol of hypochlorite) of sodium hypochlorite bleach and 2 N hydrochloric acid are added simultaneously, while stirring, in such a way that the pH of the reaction mixture remains within the range of 11 to 11.5. The operation requires 30 to 40 minutes.

In variant B, the gel according to variant A is treated with 19.5 g of sodium cyanide (0.4 mol). Chlorine is then passed in at 5°C while stirring and the pH-value is kept at 11 to 11.5 by simultaneous addition of 2 N sodium hydroxide solution. The operation is stopped after 200 ml of sodium hydroxide solution (0.8 mol) have been added.

In variant C, 2.45 g of sodium cyanide (0.05 mol) are dissolved in the starch gel according to variant A. The mixture is cooled to 5°C and chlorine is introduced slowly (in bubbles) while stirring, the pH-value being kept at about 11 by continuous addition of a solution of 22 g (0.45 mol) of sodium cyanide in 300 ml of 2 N sodium hydroxide solution. The amount of chlorine passed in corresponds approximately to 0.3 mol of sodium hypochlorite.

In variant D, 20 g of potato starch of the same quality are suspended in 800 ml of water at 30° to 40°C, the mixture is warmed to 60°C over the course of 30 minutes, the transparent gelatinous mass is cooled to 5°C, 25 ml of a solution of 25.5 g (0.52 mol) of sodium cyanide in water (total volume 245 ml) are added, the mixture is stirred slowly and the following are added simultaneously over the course of about one hour: 220 ml (0.44 mol of sodium hypochlorite) of sodium hypochlorite bleach and the remaining 220 ml of the above solution of sodium cyanide.

After completion of the reaction, the pH-value is between 13 and 14. The mixture is filtered at 15°C, the product is washed with water until free of chlorine (2 l) and a filter cake of 157 g is obtained. Its dry weight is 22.6 g and its nitrogen content 6.4%, relative to the dry weight.

In variant E, the procedure followed is exactly as in variant D, but a solution of 49 g (1 mol) of sodium cyanide (total volume 245 ml) is used. The result is practically identical with the result of variant D (weight of the filter cake, dry weight and nitrogen content) except that in this case the filtrate and the wash water contain 0.54 mol of unchanged cyanide. Thus, the cyanide consumption corresponds to the amount of hypochlorite employed.

In a completely identical parallel experiment, a continuous test of the behaviour of a small sample of the reaction mixture in acetic acid medium towards potassium iodide/starch paper was carried out. A blue colouration regularly occurred if the molar ratio of added hypochlorite to cyanide exceeded a value of 0.46. In an alkaline medium the blue colouration only manifests itself, as is known, when the said ratio exceeds a value of 1. The significance of this difference hitherto remains unclear. Possibly the blue colouration in an acetic acid medium is an indication of an intermediate product which always disappears again if the molar ratio falls below 0.46. It cannot be cyanogen chloride because cyanogen chloride does not produce a colour with the potassium iodide/starch reagent. Equally, it is not unconsumed hypochlorite since the latter colours the reagent even in an alkaline medium.

A sample of the lyophilised product in potassium bromide absorbed between 3,200 and 3,600 cm$^{-1}$ (OH band) somewhat more weakly than the starch used as the starting material and also had a weak but distinct absorption at 2150 cm$^{-1}$ (allocation uncertain: cyanate?$>$C=NH?) and a strong absorption at 1720 cm$^{-1}$ ($>$C=N-band).

16. A note on the starch quality

Not every industrial starch is as such suitable for cross-linking, and activation for amine fixing, in accordance with the invention. It is indeed not surprising that the starting material on the one hand, and the method of extraction and digestion on the other, influence the accessibility and the activity of the hydroxyl groups which are involved according to the invention. The conditions are here thus similar to those in the case of cellulose powders and cellulose fibres.

II. The amine fixing reaction

Representative examples are provided by the fixing of an acylase which is offered by Messrs. Amano Pharmaceutical Co. Ltd., Nagoya (Japan) for the industrial racemate splitting of N-acetylated α-aminoacids, the fixing of crystalline chymotrypsin and the fixing of valine and of glutamic acid.

In extensive preliminary experiments with the acylase mentioned it was found that it is advantageous to store the activated products at 4° or −15°C. On the other hand, losses in activity at room temperature are insignificant over the course of 48 hours in the moist state. In the lyophilised state, the storage temperature does not play a major role. The acylase is fixed in water or 0.1 N bicarbonate solution with addition of 10$^{-4}$ M cobalt chloride solution somewhat more effectively than in 0.1 N bicarbonate solution. If the ionic strength is increased by adding sodium chloride (0.1 N or 0.5 N), the fixing increases somewhat. The dilution is of greater importance: in mixtures of 1 g of lyophilised active carrier and 0.1 g of acylase in 5, 20 or 50 ml of water the fixing was 84, 79 and 68% of the activity introduced. The ratio of carrier to enzyme also plays an important role: 10 g portions of moist carrier were incubated for 72 hours at 4°C with 0.02, 0.05, 0.1 and 0.2 g of enzyme in 10 ml of 0.1 N bicarbonate solution and 10$^{-4}$ M cobalt chloride solution. After elution with one liter of the same buffer in each case, the determination of the activity in the filtrate showed that the fixing was 100, 100, 77.3 and 83.5%.

The fixing takes place relatively slowly: 5 g portions of moist carrier, 0.1 g of acylase and 5 ml of water were incubated at 4°C for 1, 2, 12 and 24 hours. After filtration and elution, the filtrate was found to contain 46, 47, 39, 27 and 13% of the activity employed.

The most effective method appears to be the method already proposed in the introduction, namely to stir the enzyme which has been lyophilised, or otherwise dehydrated as possible, into the moist filter cake obtained on filtration of the activated carrier, in which case it can be of advantage first to suspend the filter cake in the buffer, to remove the excess buffer by filtration and to use the filter rcake which is now buffered.

17. Acylase, fixing test

The moist filter cakes from 100 mg portions of water-soluble starch from Examples 1, 2, 4, 5, 6 and 7, from 100 mg of sucrose according to Example 9 and from 100 mg of polyvinyl alcohol according to Example 10 are mixed with 25 mg of an enzyme preparation which was obtained by dialysis of "Amano" acylase and lyophilisation of the non-dialysable constituent, the mixtures are left to stand overnight in the cold and washed with 200 ml of the above-mentioned bicarbonate/cobalt chloride buffer, and the activity is tested by adding a standard solution of the sodium salt of acetyl-DL-phenylalanine. A pre-treatment of the filter cake with the buffer mixture proves superfluous in most cases.

The filter cakes according to Example 3 and the fibres according to Example 11 and 12 are treated analagously.

18. Acylase, use test 1 g of lyophilised acylase which has been prepurified by dialysis is stirred into the moist filter residue (activated "amylopectin fraction" from 10 g of potato starch and 9 g of sodium cyanide) which contains a little base and a little $Co^{++}$ ion from the washing process (0.1 M $NaHCO_3$ + $10^{-4}$ M $CoCl_2$). The mixture is left to stand overnight at 4°C, taken up in 0.1 M $NaHCO_3$ + $10^{-4}$ M $CoCl_2$ and filtered, and the product is slowly and thoroughly rinsed with 1 liter of the same salt solution. The filter residue, which is now charged with acylase, is added to a solution of 24 g of sodium acetyl-DL-phenyl-alanine in 300 ml of $10^{-4}$ M $CoCl_2$ and is incubated, with slow stirring, at 40°C in the presence of a little thymol. After 2 days, during which the progress of the reaction can be followed polarimetrically, the fixed enzyme is filtered off and the filter residue — without eluting it — is introduced into a further portion of 24 g of sodium acetyl-DL-phenylalanine in 300 ml of $10^{-4}$M $CoCl_2$ (2nd degradation cycle).

L-Phenylalanine crystallises from the concentrated filtrate in acetyl-phenylalanine, yield of 60 – 70% and acetyl-phenylalamine, yield 70 – 80%, which predominantly consists of the D-form, crystallises from the acidified mother liquor. The losses of substance are attributable to the liquid retention by the voluminous filter residue. The losses already diminish when working up the filtrate from the second degradation cycle. At least 100 to 150 degradation cycles can easily be carried out before the enzyme inactivation requires replacing the enzyme preparation. The fixed acylase can be kept unchanged for months in the cold, especially in the presence of sodium acetate and sodium acetyl-D-phenyl-alanine.

19. Chymotrypsin

A mixture of 25 mg of chymotrypsin and 25 mg of sodium sulphate is dissolved in 2 ml of water and lyophilised, and the residue is ground, with addition of 2 ml of 0.1 N sodium bicarbonate solution, with a filter cake obtained according to Example 1, at 0° to 5°C, from 200 mg of soluble starch, 200 mg of sodium cyanide, 20 ml of water and 4 mmols of sodium hypochlorite (bleach), the whole is left to stand for 30 hours at room temperature and is very thoroughly washed with 1.5 l of water, and the residue is lyophilised: dry weight approx. 220 mg containing 11.5% of water (Karl Fischer titration). A sample was hydrolysed for 36 hours at 110°C in 20% strength hydrochloric acid and the hydrolysis product was analysed for aminoacids according to Stein and Moor. The expected aminoacids were found in the expected ratio; their total amount corresponded to a fixing of 16.5 mg of chymotrypsin.

20. Valine on soluble carrier

1%, of the weight of the solution, of valine is added to the dialysed solutions according to Example 8 and Example 14, the mixture is buffered to pH 9 with a little bicarbonate and is left to stand overnight at 0°C, dialysed at 0°C in order to remove the sodium ions completely, and lyophilised. The hydrolysate of the lyophilised products contains valine.

21. Glutamic acid on insoluble carrier 1 l portions of filter cake prepared according to the main instruction in Example 15 were treated in various dilutions, at various temperatures and for various times, with 8 g of glutamic acid (54 mmols) and 5.6 g of sodium carbonate (54 mmols). The charging achieved increases by a factor of 6.5 in the concentration range of 0.01 to 0.1 g of glutamic acid per ml, by a factor of 1.3 from 0° to 20°C, by a factor of 1.16 from 20° to 40°C, by a factor of 1.17 from 2.5 to 5 hours and by the same factor again from 5 to 50 hours. At constant volume, it increases three and a half-fold on increasing the amount of glutamic acid five-fold. On dilution with 20 ml of water, working at room temperature with a 15-hour reaction time, an average of 10 mmols of glutamic acid was fixed (as determined acidimetrically and by aminoacid analysis according to Stein and Moore). The fixed glutamic acid consumes 1 mol of alkali per mol; its titration curve is reminiscent of that of monosodium glutamate in the presence of formaldehyde.

III. ANALYTICAL DEMONSTRATION OF FIXED ENZYME ACTIVITY

22. Fixed acylase

A filter cake or a quantity of fibres corresponding to 100 mg of originally employed polyhydroxy compound is taken up in 4 ml of $10^{-4}$ M cobalt chloride solution, warmed to 40°C and treated with 4 ml of a solution, warmed to 40°C, which contains DL-acetylphenylalanine ($4.5×10^{-3}$ M), sodium bicarbonate ($6.6×10^{-3}$ M) and cobalt chloride ($10^{-4}$ M). The mixture is incubated for 30 minutes at 40°C while stirring and is filtered, and 5 µl of the filtrate are applied to a thin layer of silica gel, alongside 5 µl of comparison solutions which contain the correct amount of phenylalanine to give spots on the chromatogram which correspond to an enzymatic degradation of 5, 10, 20 and 40%. The migrating agent is chloroform/methanol/glacial acetic acid/pyridine (70/25/5/5). The degree of enzymatic degradation, estimated in this way, was between 5 and 40% in the case of all embodiments described in the examples.

23. Fixed chymotrypsin

A solution of 20 mg of acetyl-L-tyrosine ethyl ester in 3 ml of ethanol is added to 9 ml of 0.1 N phosphate buffer (pH 7.8), the enzyme preparation is added, the pH-stat is connected up and the reaction is followed by examining the consumption of 0.2 N sodium hydroxide solution at 27° – 28°C. The activity of the preparation from Example 19 was about half as great as was to be expected from the amount of chymotrypsin fixed.

APPENDIX

1. Experimental comparison of reaction routes I and II

Reaction routes I and II according to the scheme given earlier are discussed in the following.

In the course of I, a certain amount of acid is liberated because of the reaction:

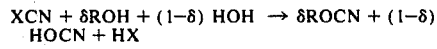

In the course of II, on the other hand, a certain amount of alkali metal hydroxide is liberated, independently of the mechanism, because of the reaction:

$$NaOCl + NaCN + \delta ROH + (1-\delta)HOH \rightarrow$$
$$\delta ROCN + (1-\delta)NaOCN + \delta NaOH + NaCL$$

Furthermore, hypochlorite contains a little free alkali metal hydroxide. Both the acid and the alkali can, in the present case, be counteracted by the presence of strong carbonate buffer to the extent that the pH shifts lie within the limits of only 0.3–0.4 pH units. Regulating the pH by means of a pH-stat had to be ruled out because of the high reaction velocities.

The high salt concentration due to the buffer slows down both I and II. The lowering of the reaction temperature from 20° to 0°C has a similar effect. I and II become conveniently comparable by the cumulative effects of these factors. The comparison experiments given below are typical with regard to reaction conditions and results:

A stock solution of
    5 ml of 2% strength starch solution (weight/weight)
    10 ml of 2 M $K_2CO_3$
is mixed with
either
    10 ml of water
    1.17 g of NaCl (20 mmols)
    5 ml of 1 M $KHCO_3$
    138 mg of NaCl (2.34 mmols)
    thus giving solution A, pH 10.55
or
    10 ml of 2 M $K_2CO_3$
    5 ml of 1 M $KHCO_3$
    138 mg of NaCl (2.34 mmols)
    thus giving solution B, pH 11.1
or
    10 ml of water
    1.17 g of NaCl (20 mmols) or 2.84 g $Na_2SO_4$
    5 ml of 1 M $KHCO_3$
    128 mg of NaCN (2.6 mmols)
    thus giving solution C, pH 10.6
or
    5 ml of water
    293 mg of NaCl (5 mmols)
    10 ml of 2 M $K_2CO_3$
    138 mg of NaCl (2.34 mmols)
    thus giving solution D, pH 12.0.

Solutions A, B, C and D are cooled to −1°C and 3 ml (2.6 mmols) of a freshly prepared aqueous solution of freshly prepared cyanogen chloride are added dropwise over the course of 1 minute, with vigorous stirring, to A or B or D (process according to I), and 2.53 g (2.34 mmols of NaOCl) of bleach are added dropwise to C (process according to II). A and B (process I) react slightly exothermically; the temperature is kept at about 0°C by cooling. After 13 minutes, the odour of the cyanogen chloride is still faintly detectable; the pH-value is about 10.25 (A) or 10.8 (B). An insoluble cross-linking product does not separate out. C (process II) gives a strongly exothermic reaction; the temperature rises transiently to +3°C in spite of cooling. The reaction mixture becomes milky even before completion of the addition of hypochlorite and thereafter the cross-linking product separates out, within seconds, in a flocculent readily filterable form. A sharp odour disappears rather rapidly. 13 minutes after the beginning of the experiment the pH-value is 11.0. The experiment with solution D serves to check the quality of the cyanogen chloride; the milky turbidity typical of cross-linking occurs even before completion of the addition of the cyanogen chloride and the cross-linking product then flocculates within seconds. The mixture is kept at about 0°C for a further 12 minutes; the pH-value is about 11.2. As expected, the odour of cyanogen chloride disappears more rapidly than in the case of the experiments with solutions A and B.

Comments: It should be noted that I in case B takes place within the pH range of II in case C. The difference in results leads to the inescapable conclusion that the cross-linking observed according to II is not attributable to the action of transiently formed cyanogen chloride. The yield and amine fixing capacity of the product obtained according to II using solution C lie within the limits generally customary for process II.

2. Note on the nature of the chemical reaction which, according to the invention, leads to cross-linked polyhydroxy compounds with amine fixing capacity.

A further indication, independent of the above result, of the different nature of I and II results from the observation that II shows the behaviour which would be expected if the first step consisted of an esterification of hydroxyl groups of starch with hypochlorous acid. This is because if a mixture of 2% strength (weight/weight) starch solution and 7% strength (weight/weight) sodium hypochlorite solution, mixed in the ratio of 100 mg of starch: 2 mmols of NaOCl, is added dropwise at 0° to 5°C, with vigorous stirring, to a well-cooled 1% strength solution of sodium cyanide, a prompt flocculation of cross-linked starch having outstanding amine fixing capacity takes place independently of the stoichiometric ratio of $OCl^-$ to $CN^-$. If, conversely, the cyanide is added dropwise to the mixture of starch and hypochlorite, a cross-linking product does not precipitate. Evidently, the cyanide is taken up by the hypochlorite before the starch can react. If, however, the stoichiometric amount of cyanide solution is poured all at once over the starch/hypochlorite mixture, flocculation of cross-linking product which is capable of fixing amine takes place, with the striking proviso that the starch-hypochlorite mixture must, before addition of the cyanide, first have been incubated for a short time, for example for 5 – 15 minutes at 20°C. In the course thereof, a part of the cyanide evidently has the opportunity of reacting directly with a part of the hypochlorite which is presumably bound to starch, for example according to the equation:

$$ROCl + CN^- \rightarrow ROCN + Cl^-$$

Accordingly, a polyhydroxy compound (dry weight 100 mg) which has been swollen in water but is insoluble therein, such as, for example, Sephadex G 200 or mercerised cellulose (Avicel) can be incubated with hypochlorite solution (2 mmols of NaOCl) for 15 to 30 minutes at room temperature, optionally with addition of solid carbon dioxide, and separated from the liquid after addition of 100 ml of water (centrifuge). The residue can be taken up in 100 ml of water, the liquid can be decanted (centrifuge), and the residue can be covered with 10 ml of 1% strength sodium cyanide solution and subsequently washed on a centrifuge until free of cyanide. The product possesses an amine fixing capacity which depends on the duration of the incubation with the hypochlorite.

The very particularly gentle and uniform cross-linking reaction, described under the examples, resulting from the action of t-butyl hypochlorite on a mixture of soluble starch and sodium cyanide would, according to this, possibly have to be interpreted as a result of a primary trans-esterification reaction between the organic hypochlorite and the starch.

What is claimed is:

1. Process for the manufacture of reaction products from a water-soluble amino compound which is capable of substitution on at least one basic nitrogen atom, and an activated carrier,
   wherein (a) (1) a cyanide compound selected from the group consisting of hydrocyanic acid and alkali metal cyanides and (2) a reagent containing positive halogen selected from the group consisting of hypochlorous acid, hypobromous acid, water-soluble salts of hypochlorous acid, water-soluble salts of hyprobromous acid, chlorine compounds which on hydrolysis yield hypochlorous acid, bromine compounds which on hydrolysis yield hypobromous acid and mixtures of said reagents, are allowed to act on a water-soluble or water-swellable polyhydroxy compound in an alkaline medium,
   b. the reaction mixture is freed of low molecular constituents,
   c. the resultant cross-linked activated product is allowed to act, in the presence of water, at a temperature below about 50°C, on the water-soluble amino compound, and
   d. dialysable material or material which has remained in dissolved form in the resultant reaction product is dialysed or filtered or washed out of the reaction product by means of water or an aqueous salt solution.

2. A process as claimed in claim 1, wherein the reaction between the polyhydroxy compound, total amount of cyanide compound and reagent containing positive halogen is carried out in a pH range of about 10 to about 13.

3. A process as claimed in claim 1, wherein the amino compound is selected from the group consisting of proteins, polypeptides, oligopeptides, aminoacids and amines of the formula:

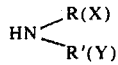

in which R(X) denotes hydrogen or a radical with hydrogen or a functional group in position X and R'(Y) denotes a radical with hydrogen or a functional group in position Y.

4. A process as claimed in claim 3, wherein step c is carried out in a neutral or weakly or moderately alkaline pH range at a temperature no higher than room temperature..

5. A process as claimed in claim 4, wherein an excess of the amino compound is used in step c.

6. A process as claimed in claim 4, wherein step c is carried out in the presence of a mixture of water and sodium bicarbonate.

7. A process according to claim 4, wherein step c is carried out in the presence of a mixture of water and sodium carbonate.

8. A process as claimed in claim 1, wherein the step a is carried out under cold conditions.

9. A process as claimed in claim 1, wherein the step c is carried out under cold conditions.

10. A process as claimed in claim 1, wherein the cyanide compound is used in a total amount of about 0.25 to 6 gram equivalents of cyanide per gram equivalent of hydroxyl groups organically bonded to the polyhydroxy compound.

11. A process as claimed in claim 1, wherein the reagent containing positive halogen is used in a total amount of from about 0.25 to 6 gram equivalents of positive halogen per gram equivalent of hydroxyl groups organically bonded to the polyhydroxy compound.

12. A process as claimed in claim 11, where the reagent containing positive halogen is a nitrogen compound containing positive halogen bonded to the nitrogen atom thereof and which can be hydrolysed to a hypohalous acid.

13. A process as claimed in claim 12, wherein the reagent is N-chloracetamide, N-chlorosuccinimide, chloramine, N-bromoacetamide, N-bromosuccinimide or the sodium salt of p-toluene sulphonic acid chloramide (Chloramine T).

14. A process as claimed in claim 11, wherein the reagent containing positive halogen is an ester of a hypohalous acid which can be hydrolysed to the hypohalous acid.

15. A process as claimed in claim 14, wherein the reagent is an alkyl hypochlorite containing 2 to 5 carbon atoms in the alkyl radical.

16. A process as claimed in claim 11, wherein the reagent containing positive halogen is an alkali hypohalite or a halogen and an alkali metal hydroxide.

17. A process as claimed in claim 16, wherein at least about 2 gram mols of alkali metal hydroxide are used per gram mol of chlorine or bromine.

18. A process as claimed in claim 16, wherein the alkali hypohalite is sodium hypochlorite bleach or potassium hypochlorite bleach.

19. A process as claimed in claim 1, wherein the total amounts of the cyanide compound and the polyhydroxy compound are admixed and the resulting mixture is treated with the reagent containing positive halogen.

20. A process as claimed in claim 1, wherein the total amount of the cyanide compound is treated with a mixture of the polyhydroxy compound and the reagent containing positive halogen.

21. A process as claimed in claim 20, wherein the mixture of polyhydroxy compound and salt of hypohalous acid, as the reagent containing positive halogen, is initially treated with carbon dioxide.

22. A process as claimed in claim 1, wherein the water-soluble amino compound is a biologically active water-soluble amino compound.

23. A process according to claim 1, wherein the reaction mixture resulting from step a is neutralized before carrying out step b.

24. A process according to claim 1, wherein step c is carried out in the presence of water and a buffer system.

25. A process according to claim 1, wherein the reaction mixture is freed of low molecular constituents by clarification and dialysis when the reaction mixture is a solution.

26. A process according to claim 1, wherein the reaction mixture is freed of low molecular constituents by clarification and gel filtration when the reaction mixture is a solution.

27. A process according to claim 1, wherein the reaction mixture is freed of low molecular constituents by filtration when the reaction mixture is a suspension.

28. A process according to claim 1, wherein the reaction mixture is freed of low molecular constituents by centrifuging and washing out when the reaction mixture is a suspension.

* * * * *